United States Patent
Scheuch et al.

(10) Patent No.: US 6,401,710 B1
(45) Date of Patent: Jun. 11, 2002

(54) DEVICE FOR CONTROLLED INHALATIONAL ADMINISTRATION OF CONTROLLED-DOSAGE DRUGS INTO THE LUNGS

(75) Inventors: Gerhard Scheuch, Gemünden; Knut Sommerer, München, both of (DE)

(73) Assignee: GSF-Forschungszentrum (DE)

( * ) Notice: Subject to any disclaimer, the term of this patent is extended or adjusted under 35 U.S.C. 154(b) by 0 days.

(21) Appl. No.: 09/323,303

(22) Filed: Jun. 1, 1999

(30) Foreign Application Priority Data

Jun. 17, 1998 (DE) .......................... 198 26 933
Nov. 6, 1998 (DE) .......................... 198 51 279

(51) Int. Cl.$^7$ ............................................ A61M 11/00
(52) U.S. Cl. ............................. 128/200.21; 128/200.22
(58) Field of Search ........... 128/200.17, 200.21–200.23, 128/203.21–203.24, 202.25, 202.26, 203.17, 203.28, 205.12–205.17, 205.24; 604/58

(56) References Cited

U.S. PATENT DOCUMENTS

| | | | | |
|---|---|---|---|---|
| 3,136,312 A | * | 6/1964 | Gattone | 128/203 |
| 3,888,252 A | * | 6/1975 | Side et al. | 128/266 |
| 4,484,577 A | * | 11/1984 | Sackner et al. | 128/203.28 |
| 4,821,712 A | * | 4/1989 | Gossett | 128/205.15 |
| 4,883,051 A | * | 11/1989 | Westenskow et al. | 128/204.21 |
| 5,203,323 A | * | 4/1993 | Tritle | 128/200.23 |
| 5,427,091 A | * | 6/1995 | Phillips | 128/205.15 |
| 5,579,760 A | * | 12/1996 | Kohler | 128/203.15 |
| 5,628,305 A | * | 5/1997 | Melker | 128/202.29 |
| 5,762,063 A | * | 6/1998 | Coates et al. | 128/205.13 |
| 5,775,320 A | * | 7/1998 | Patton et al. | 128/200.14 |
| 5,975,078 A | * | 11/1999 | Pauley | 128/205.23 |
| 6,062,213 A | * | 5/2000 | Fuisz et al. | 128/200.21 |
| 6,158,428 A | * | 12/2000 | Mecikalski | 128/200.23 |

FOREIGN PATENT DOCUMENTS

| | | | |
|---|---|---|---|
| GB | 2104394 A | * | 8/1982 |
| GB | 2137886 A | * | 10/1984 |
| GB | 2145335 A | * | 3/1985 |
| GB | 2182249 A | * | 5/1987 |
| WO | WO 88/03419 | * | 5/1988 |

OTHER PUBLICATIONS

Aerosol Age; Aerosloized Drug Delivery Accessories, 1984 (Figure 1, p. 25).*
Eur J Respir Dis (1987), 70, 234–238; "Aerosol–in–bag" Administration of Inhaled Bronchodilators, Feisal A. El–Kassimi.*
Journal of Asthma, 1984, 21(4), 265–270 (fig. 1 and 2); Evaluation of Bronchodilation from Aerosol Beta2 Agonists Delivered by the Inhal–Aid Device to Young Children, William Huntley, RRT and Miles Weinberger, MD.*

* cited by examiner

Primary Examiner—John G. Weiss
Assistant Examiner—Teena Mitchell
(74) Attorney, Agent, or Firm—Myers Bigel Sibley & Sajovec

(57) ABSTRACT

The invention relates to a device for controlled inhalational administration of controlled-dosage drugs into the lungs, comprising a closed recipient adapted to be charged with a predeterminable aerosol volume and from which the aerosol may be withdrawn by means of a control means for controlling the inhalant flow.

14 Claims, 1 Drawing Sheet

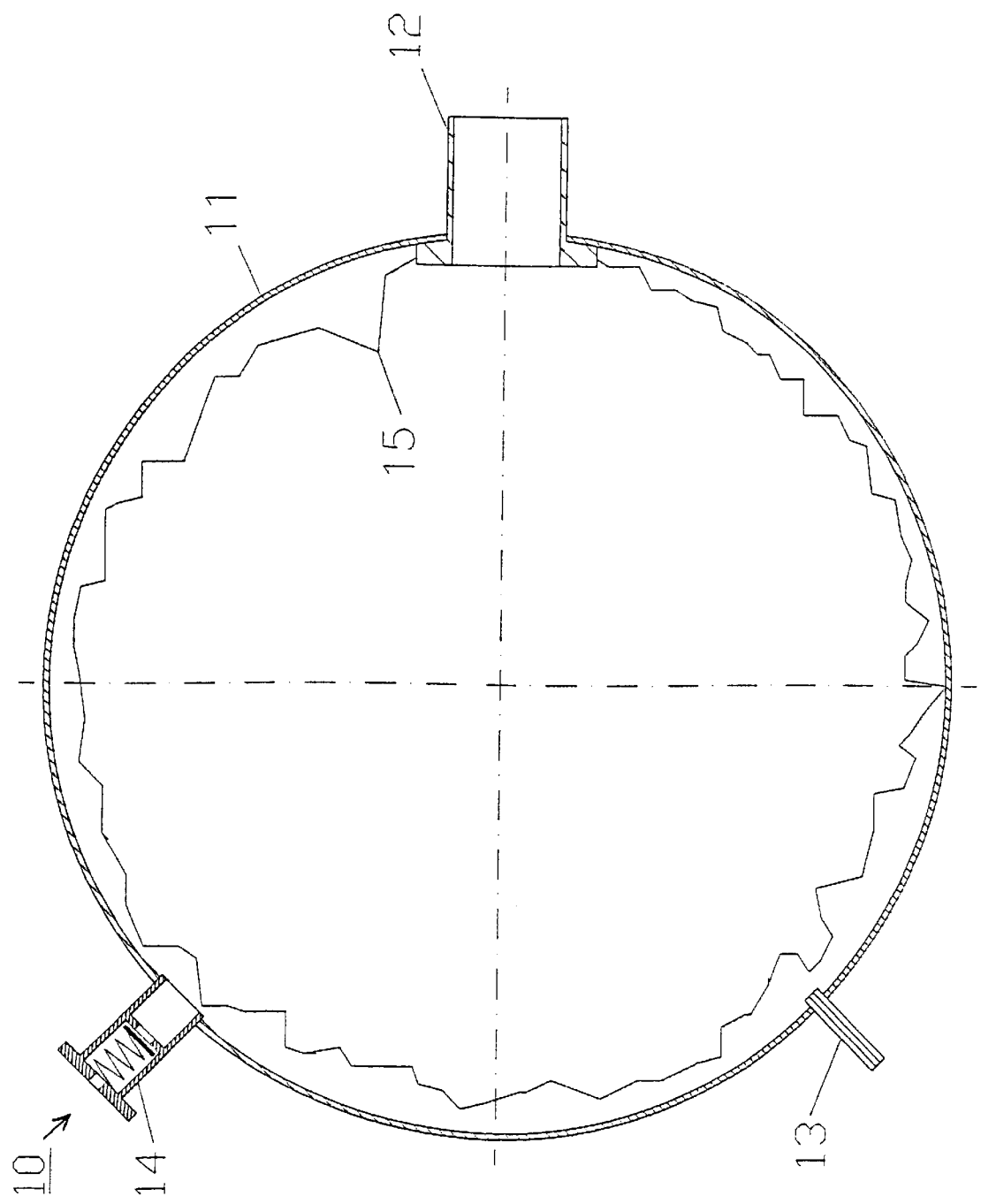

DEVICE FOR CONTROLLED INHALATIONAL ADMINISTRATION OF CONTROLLED-DOSAGE DRUGS INTO THE LUNGS

FIELD OF THE INVENTION

The present invention relates to a device for controlled inhalational administration of controlled-dosage medicated aerosols into the lungs.

BACKGROUND OF THE INVENTION

The application of medicaments in the form of aerosols by inhalation into the human lungs is gaining an ever-increasing importance. It entails the problem that a rapid inhalation promotes the deposition of particles on the larynx and in the mouth and prevents the aerosol particles from penetrating into the lungs. What is moreover inexpedient is the fact that the aerosol to be applied is not quantified because it is specifically the inhalation, which should be controlled whenever possible and should be slow in particular, which promotes the deposition of the aerosol particles in the lungs. When the patient is able to breathe at any respiration rate desired the disadvantageous situation arises that the deposition of the particles in the lungs always presents a wide range of variation. With uncontrolled inhalation using supply reservoirs so far known (spacers) the patient varies both the flow (i.e. the respiration rate) and the volume of each breath.

SUMMARY OF THE INVENTION

The present invention is therefore based on the problem of improving a device of the general type outlined by way of introduction in a way such that with a simple manipulation an unproblematic controlled inhalation will be possible.

In accordance with the present invention this problem is solved by a device for controlled inhalational administration of controlled-dosage drugs into the lungs, comprising a closed recipient adapted to be charged with a predeterminable aerosol volume and from which the aerosol may be withdrawn by means of a control means for controlling the inhalant flow. Preferred features improving the invention in an expedient form are evident from the dependent patent claims.

The inventive provisions allow for a limitation of the respiratory flow in an expedient manner, which permits the adjustment of a maximum inhalant flow inhaled by the patient, with the deposition of aerosol particles in the lungs being increased. Due to different limitations of flow (e.g. by means of a critical nozzle, adjustable nozzle) it is possible to set the flow at different rates so that it will also be possible to achieve an adaptation to the administered drugs and to the patient's capabilities.

For a limitation of the volume which can be inhaled a recipient is provided, preferably in the form of a balloon or bag, with a quantifiable aerosol amount being adjustable by the predetermined initial charge in the recipient.

It is moreover expedient that the patient's co-ordination is limited by the inventive device in so far as initially a certain charge is defined and then discharged calmly. Moreover, due to a preferably transparent structure of the recipient or balloon, respectively, the patient can also visually check in an expedient way whether he has actually withdrawn the defined volume, and he is moreover able to follow up individual inspirations by shrinkage of the balloon.

Different volumes can be pre-selected for individual fields of application in an expedient manner, e.g. 50 to 150 ml for the preferred deposition in the conductive respiratory tract of the lungs, or 500 to 5000 ml for a preferred maximum deposition of the aerosol in the alveolar region of the lungs.

The structure of the device is extraordinarily simple to check and is presented to the patient in a form which does not disconcert him with a complex electronic system, thus promoting the general acceptance in a self-explaining form (visible discharge of a balloon).

In the inventive device the recipient, which is configured as a bag or balloon, is charged with a defined aerosol quantity which is predetermined by the size of the recipient. The aerosol can be produced in a conventional manner by metered-dosage aerosols, dry powder inhalators, ultrasonic or atomiser systems. In correspondence with a preferred embodiment of the invention, a balloon is disposed in a transparent recipient, e.g. of Plexiglas, which permits a comfortable operation by the patient due to its shape, e.g. with a handling element in the form of a recessed grip.

The patient then inhales the contents of the bag, with an adjustable valve or a critical nozzle, respectively, which forces him to discharge the bag slowly. This inhalation flow can be varied by adjustment of a critical nozzle or an adjustable valve whilst the patient can directly visually check the amount of the inhaled aerosols insofar as after inspiration of a quantified predetermined amount of the aerosol the bag is empty.

Depending on the application, various volumetric sizes are envisaged for the housing. If, for instance, the aerosol should be deposited exclusively or preferably in the conductive respiratory tract small housings with volumes in the range from 50 to 250 ml are advisable whereas when the deposition is demanded mainly or exclusively in the alveolar region housings with volumes between 600 and 5000 ml may be provided. Here the rule applies that the aerosol arrives in the alveolar region the more efficiently and in a higher quantity, the deeper inhalation is.

In correspondence with the claimed features it is hence expedient to dispose the recipient in a housing which may be transparent, at least partly, for a check of the charging level in the recipient, with the recipient being connected to an inhalation mouthpiece and with the housing being provided with a charging valve. The means for adjusting the inhalant flow is designed to include an adjusting valve or a so-called critical nozzle.

The recipient has, at least partly, an elastic configuration, preferably it resumes elastically its initial shaped and preferably it is designed in the form of a bag or balloon whilst the housing is provided with a handling element which is preferably integrated into the shape of a handle. This handling element may preferably be designed as recessed grip whilst the charging valve is expediently disposed in the region of this handling element.

The invention will now be described in more details in the following by the example of an embodiment which is schematically illustrated, with reference to the attached FIGURE.

The attached FIGURE shows a schematic cross-sectional view of one embodiment of an inventive device 10. The device 10 consists of a spherical housing 11 which is made of a transparent material such as Plexiglas. The housing 11 moreover presents a projecting mouthpiece 12, a critical nozzle 13 configured as thin connecting sleeve having a small cross-section of flow for limiting the flow rate, as well as a valve 14 which is designed as one-way valve and opens from the interior space of the container 11 to the outside. Inside the container as such a recipient is schematically indicated in the form of a balloon 15 which is closed and connected to the mouthpiece 12.

For application of the device initially a volume of the medicated aerosol to be administered is defined and then the balloon 15 is appropriately charged via the mouthpiece 12, with the valve 14 permitting the expansion of the balloon 15 inside the transparent container 11.

For performing the desired inhalation the patient now grasps the housing by a handling element which is not illustrated here, expires and takes the mouthpiece 12 into his mouth (upon removal of a sealing sheet). For inspiration then the critical nozzle 13 is released for controlled discharge of the aerosol from the balloon 15. An adjustable valve may also be provided instead of the critical nozzle, with the cross-section of flow of the critical nozzle determining the admission of outside air into the interior space of the container 11 and hence the possible contraction of the balloon 15 so as to allow for a simple control of the tidal volume. At the same time, a volume of medicated aerosol to be administered is determined via the charging level in the balloon directly; when an adjustable valve is used instead of the critical nozzle 13 it is also possible to determine the depth of the respective breath and hence the desired region of application of the medicated aerosol.

In a preferred embodiment of the device for controlled inhalational administration of controlled-dosage drugs into the lungs, the recipient 15 has such a resilient design that after withdrawal of the aerosol it will automatically resume the original shape it had prior to withdrawal. In this manner it is easily possible to charge the discharged recipient 15 with drugs/aerosols from the outside via the inhalation mouthpiece.

A sealing sheet, which is not illustrated here, is applied on the mouthpiece 12 for sealing and for hygienic protection of the charged recipient 15, and is removed prior to use.

The device can be manufactured with a Plexiglas housing and a rubber balloon in an extraordinarily simple manner within a price range reaching a level as low as the price level of disposable articles.

What is claimed is:

1. A device for controlled inhalational administration of controlled-dosage drugs into the lungs, said device comprising;
    a housing;
    a closed recipient disposed inside said housing and adapted to be charged with a predeterminable volume of an aerosol; and
    a control means operative to limit a flow rate of air into said housing and between said housing and said recipient to control a rate of contraction of said recipient and thereby an inhalant flow from said recipient;
    wherein said aerosol may be withdrawn from said recipient and said recipient includes an elastic material that resumes an original shape after withdrawal of at least some of said aerosol.

2. A device according to claim 1, wherein said control means comprises an adjusting valve.

3. A device according to claim 1, wherein said control means comprises a nozzle.

4. The device according to claim 3 wherein said nozzle includes a thin connecting sleeve having a small cross-section of flow for limiting said flow rate.

5. A device according to claim 1, wherein said recipient is connected to an inhalation mouthpiece.

6. A device according to claim 1, wherein said recipient is at least partly elastic.

7. A device according to claim 1, wherein said recipient includes at least one of a bag and a balloon.

8. A device according to claim 1, wherein said housing comprises a charging valve operative to allow the fluid to escape the inside of said housing from between said housing and said recipient, and wherein said control means is provided on said housing.

9. A device for controlled inhalational administration of controlled-dosage drugs into the lungs, said device comprising;
    a housing;
    a closed recipient disposed inside said housing and adapted to be charged with a predeterminable volume of an aerosol; and
    a control means operative to limit a flow rate of air into said housing and between said housing and said recipient to control a rate of contraction of said recipient and thereby an inhalant flow from said recipient;
        wherein said aerosol may be withdrawn from said recipient and said recipient includes an elastic material that resumes an original shape after withdrawal of at least some of said aerosol; and
        wherein said housing is at least partly transparent for control of a charging level in said recipient.

10. A device according to claim 9, wherein said recipient is at least partly elastic.

11. A device according to claim 9, wherein said recipient includes at least one of a bag and a balloon.

12. A device according to claim 9, wherein said housing comprises a charging valve operative to allow the fluid to escape the inside of said housing from between said housing and said recipient: and wherein said control means is provided on said housing.

13. A device for controlled inhalational administration of controlled-dosage drugs into the lungs, said device comprising:
    a housing;
    a closed recipient disposed inside said housing and adapted to be charged with a predeterminable volume of an aerosol, said recipient including at least one of a bag and a balloon; and
    a control means operative to limit a flow rate of air into said housing and between said housing and said recipient to control a rate of contraction of said recipient and thereby an inhalant flow from said recipient, said control means including an adjusting valve;
        wherein said aerosol may be withdrawn from said recipient and said recipient includes an elastic material that resumes an original shape after withdrawal of at least some of said aerosol.

14. A device for controlled inhalational administration of controlled-dosage drugs into the lungs, said device comprising;
    a housing;
    a closed recipient disposed inside said housing and adapted to be charged with a predeterminable volume of an aerosol, said recipient including at least one of a bag and a balloon;
    a control means operative to control a flow rate of air into said housing and between said housing and said recipient to control an inhalant flow from said recipient, wherein said control means is provided on the housing; and
    a charging valve operative to allow the fluid to escape the inside of the housing from between the housing and the recipient;

wherein said aerosol may be withdrawn from said recipient and said recipient includes an elastic material that resumes an original shape after withdrawal of at least some of said aerosol; and wherein said housing is at least partly transparent for control of a charging level in said recipient.

* * * * *